United States Patent
Tokhtuev et al.

(10) Patent No.: US 9,835,482 B2
(45) Date of Patent: Dec. 5, 2017

(54) GEAR FLOW METER WITH OUT OF PRODUCT SENSOR

(71) Applicant: Ecolab USA Inc., St. Paul, MN (US)

(72) Inventors: Eugene Tokhtuev, Duluth, MN (US); Christopher J. Owen, Duluth, MN (US); Anatoly Skirda, Hermantown, MN (US); Paul Simon Schilling, Duluth, MN (US); Viktor Slobodyan, Duluth, MN (US)

(73) Assignee: Ecolab USA Inc., St. Paul, MN (US)

( * ) Notice: Subject to any disclaimer, the term of this patent is extended or adjusted under 35 U.S.C. 154(b) by 194 days.

(21) Appl. No.: 14/637,586

(22) Filed: Mar. 4, 2015

(65) Prior Publication Data
US 2016/0258790 A1 Sep. 8, 2016

(51) Int. Cl.
G01F 1/08 (2006.01)
G01F 1/06 (2006.01)
G01F 3/10 (2006.01)
G01N 27/22 (2006.01)

(52) U.S. Cl.
CPC .............. G01F 1/08 (2013.01); G01F 1/065 (2013.01); G01F 3/10 (2013.01); G01N 27/226 (2013.01)

(58) Field of Classification Search
CPC .......................... G01N 2291/0224; G01F 1/74
USPC ............................................ 73/61.44, 861.04
See application file for complete search history.

(56) References Cited

U.S. PATENT DOCUMENTS

| | | | | |
|---|---|---|---|---|
| 3,006,189 A | * | 10/1961 | Warren | G01F 15/022 324/669 |
| 3,066,529 A | * | 12/1962 | Warren | G01F 15/022 310/1 |
| 3,385,108 A | * | 5/1968 | Rosso | G01F 15/0755 700/285 |
| 4,266,188 A | * | 5/1981 | Thompson | G01N 27/08 324/606 |
| 6,581,458 B1 | * | 6/2003 | Hathaway | G01F 1/08 73/238 |
| 6,755,086 B2 | * | 6/2004 | Salamitou | G01F 1/74 73/861.04 |
| 7,523,660 B2 | | 4/2009 | Albrecht | |
| 8,069,719 B2 | * | 12/2011 | Tokhtuev | G01F 3/10 73/261 |
| 8,166,828 B2 | | 5/2012 | Skirda | |
| 8,943,901 B2 | | 2/2015 | Tokhtuev et al. | |
| 2009/0126478 A1 | | 5/2009 | Moilanen et al. | |
| 2010/0089172 A1 | | 4/2010 | Boehm | |

(Continued)

OTHER PUBLICATIONS

International Search Report for International Application No. PCT/US2016/020954, dated Jun. 23, 2016, 11 pages.

*Primary Examiner* — Walter L Lindsay, Jr.
*Assistant Examiner* — Milton Gonzalez
(74) *Attorney, Agent, or Firm* — Fredrikson & Byron, P.A.

(57) ABSTRACT

Systems and methods related to a flow meter and/or flow meter operation can include one or more sensors and be capable of detecting parameters of the fluid flowing the flowmeter. One or more sensors can include capacitive sensors having a plurality of electrodes and configured to detect capacitive properties of a fluid flowing through the flow meter. Detected changes in detected properties of the fluid can be evidence of important changes in the fluid, such as an out of product event or a contamination of the fluid.

20 Claims, 11 Drawing Sheets

(56) References Cited

U.S. PATENT DOCUMENTS

2010/0199758 A1    8/2010    Tokhtuev et al.
2012/0031195 A1    2/2012    Skirda et al.

* cited by examiner

| Detectable Area | Rotation State | Non-contact Sensor ||||
|---|---|---|---|---|---|
| | | 540 | 545 | 550 | 555 |
| 542, 544 | A | 0 | 0 | 0 | 0 |
| | B | 1 | 0 | 0 | 0 |
| | C | 1 | 1 | 0 | 0 |
| | D | 0 | 1 | 0 | 0 |
| 552, 554 | E | 0 | 0 | 0 | 0 |
| | F | 0 | 0 | 1 | 0 |
| | G | 0 | 0 | 1 | 1 |
| | H | 0 | 0 | 0 | 1 |

GEAR FLOW METER WITH OUT OF PRODUCT SENSOR

FIELD

This disclosure relates to a positive displacement fluid flow meter, more particularly, to the use of a gear flow meter incorporating non-contact sensors and methods of use of such devices.

BACKGROUND

Positive displacement fluid measurement systems may be used to measure a flow rate or volume of a fluid or gas. For example, dispensing systems may use feedback from a positive displacement fluid meter to control the volume of fluid dispensed. Such control systems are often used in lieu of time-on controls to more accurately dispense precise amounts of fluid or gas and is commonly used in a variety of settings including, but not limited to, the industrial, healthcare, pharmaceutical and food and beverage industries. For example, a positive displacement fluid meter may be used in the manufacturing process of a drug which requires accurate measurement of two materials to be mixed into a single batch. The positive displacement fluid meter may be installed in the supply lines of the respective materials and feedback from the meters may be used to dispense the appropriate amount of each material into a blend tank to be mixed. This application of a positive displacement meter, like many others, may require the positive displacement meter to have an accuracy of measurement (e.g., +/−0.5%) to comply with quality control or regulations, for example. Accordingly, ensuring that a positive displacement meter accurately measures a volume of fluid or gas can help ensure that a system or process performs its intended function.

In some configurations, the positive displacement meter comprises at least one rotating element, which rotates as fluid flows through the meter. The metered amount of fluid flowing through the meter corresponds to the rotational motion and position of the rotating element. In some configurations, however, the rotating element can rotate in the meter even if the appropriate fluid is not flowing through the meter. For example, when a fluid such as a product for making a solution is pumped through the meter, the product causes the rotating element to rotate within the meter as it is pumped. Once the product runs out, air can be pumped through the meter and instead of the product. The air can cause the rotating element to rotate without product flowing through the system, thus providing a false indication of product flowing through the meter.

SUMMARY

Aspects of the invention generally relate to systems and methods including flow meters for use in a fluid flow system. In some embodiments, a flow meter includes a housing defining a chamber and a first rotating element within the chamber and configured to rotate as fluid travels through the housing. The first rotating element can include a detectable area, such as an optically detectable area configured to reflect light of a first wavelength differently than other portions of the first rotating element that are not the detectable area. The housing can include a portion that is substantially transparent to light of the first wavelength, so that light of the first wavelength can be directed into and received from inside the housing. The flow meter can include an optical assembly including an optical emitter configured to emit light at the first wavelength into the chamber via the transparent portion of the housing and an optical detector configured to detect light of the first wavelength reflected from inside the chamber.

A system for use with the flow meter can include a capacitive sensor positioned proximate the housing. The capacitive sensor can include a first electrode, a second electrode, and a first insulator separating the first and second electrodes. In some embodiments, the first and second electrodes can be configured such that an electrical potential applied therebetween can create an electric field that extends into the housing of the flow meter. The capacitance between the first and second electrodes can be used to determine various properties about the operation of the system.

A system can include a controller configured to apply an electrical potential between the first and second electrodes. The controller can be further configured to determine the capacitance between the first and second electrodes. In some examples, the controller can detect the presence of a product flowing through the flow meter housing based on the determined capacitance between the first and second electrodes. Monitoring the capacitance between the first and second electrodes can be performed to create alerts regarding the operation of the system, such as an out-of-product alert based on the analyzed capacitance.

In some embodiments, a flow meter can include a second capacitive sensor including third and fourth electrodes between which a second capacitance can be determined. The second capacitance can be compared to the first capacitance, and changes of the difference between the first and second capacitances can be monitored.

The details of one or more examples are set forth in the accompanying drawings and the description below. Other features, objects, and advantages will be apparent from the description and drawings, and from the claims.

BRIEF DESCRIPTION OF DRAWINGS

The following drawings are illustrative of particular examples of the present invention and therefore do not limit the scope of the invention. The drawings are not to scale (unless so stated) and are intended for use in conjunction with the explanations in the following detailed description. Examples of the present invention will hereinafter be described in conjunction with the appended drawings, wherein like numerals denote like elements.

DETAILED DESCRIPTION

Figure 1:
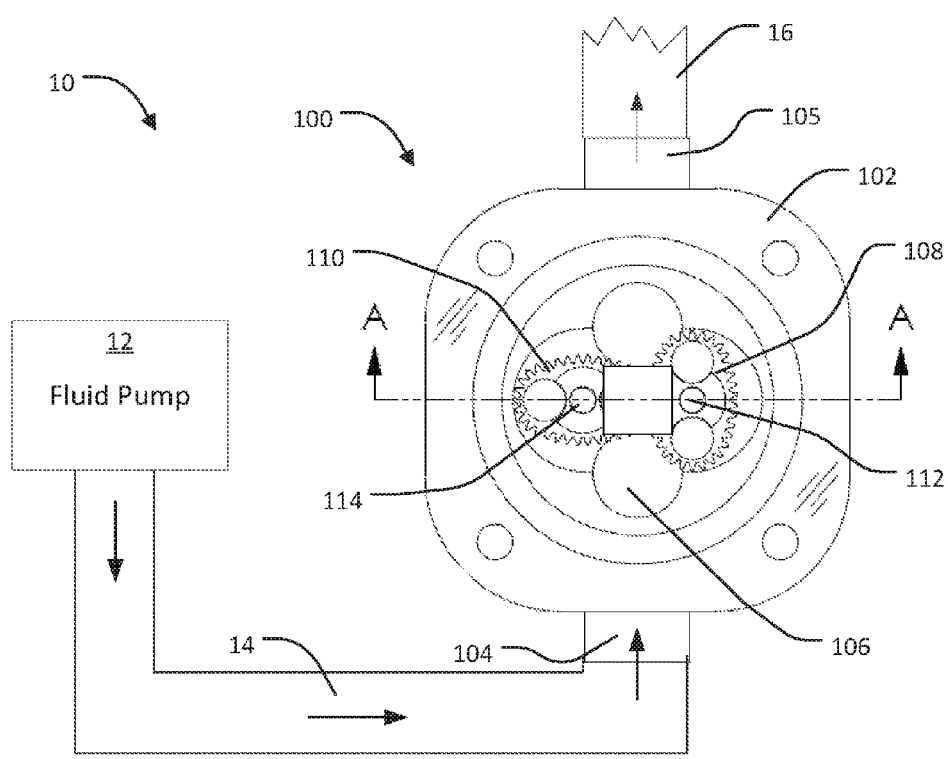
FIG. 1 is a top plan view of a fluid flow measurement system including an oval gear meter.

The following detailed description is exemplary in nature and is not intended to limit the scope, applicability, or configuration of the invention in any way. Rather, the following description provides some practical illustrations for implementing examples of the present invention. Examples of constructions, materials, dimensions, and manufacturing processes are provided for selected elements, and all other elements employ that which is known to those of ordinary skill in the field of the invention. Those skilled in the art will recognize that many of the noted examples have a variety of suitable alternatives.

Positive displacement fluid meters are used in a variety of applications to measure flow rate or volume of a fluid. For example, in the pharmaceutical industry, positive displacement meters may be used to precisely measure amounts of materials required to manufacture a drug. This application of a positive displacement meter, like many others applications, may require the positive displacement meter to have an accuracy of measurement (e.g., +/−0.5%) to comply with quality control or regulations, for example. Furthermore, positive displacement fluid meters may be used in applications with varying flow characteristics, e.g., high/low flow rates and uniform/non-uniform fluid flow. Accordingly, ensuring that a positive displacement meter accurately measures a volume of fluid, notwithstanding the flow characteristics of the application, may help ensure that the system or process performs its intended function.

Positive displacement fluid meters generally require mechanical displacement of components of the meter in order to measure flow. Gear meters, in particular oval gear meters, are an example of a positive displacement fluid meter wherein gears of the meter are displaced to measure fluid flow. An oval gear meter provides a pair of intermeshing oval gears positioned within an oval gear chamber such that the gears rotate in concert. A fluid may be measured by introducing the fluid into the chamber through a fluid inlet to cause the gears to rotate. The intermeshing of the gears prevent the fluid from passing between the gears themselves causing the fluid to pass around the gears within pockets defined between the oval gears and the chamber wall. In an oval gear, the volumes of the pockets are precisely measured so the volume of fluid exiting the chamber during each rotation is known. Thus, the volume of fluid flow through an oval gear meter may be measured by measuring the number of rotations of the gears. Likewise, flow rate may be determined from the speed with which the gears rotate.

Non-contact sensors may be included in an oval gear to measure gear rotation. Generally, a non-contact sensor may be configured to sense a detectable area located on at least one of the gears and may be located outside of the chamber in a position to sense the detectable area as the gears rotate. The non-contact sensor may also be configured to generate a detection signal based on whether the detectable area is sensed. A controller may be included in or otherwise in communication with an oval gear or non-contact sensor to receive the detection signal from the non-contact sensors and generate a rotational count. The controller may include a programmable processor and/or memory. The controller may be further configured to calculate a volume of fluid flow through the oval gear based on the rotational count.

FIG. 1 is a top plan view of a fluid flow measurement system 10 including an oval gear meter 100. System 10 includes a fluid pump 12, a first fluid line 14, a second fluid line 16 and an oval gear meter 100. First fluid line 14 may be in fluid communication with fluid pump 12 configured to provide a fluid flow through system 10. Fluid pump 12 may be in fluid communication with a fluid source (not shown) and may any suitable pump to provide a fluid flow through the system. The fluid flow may have a variety of fluid flow characteristics and may depend on the type of pump selected or the application of system 10. For example, different applications may require either a high fluid flow volume or a low fluid flow volume. Certain examples may require uniform fluid flow provided by a peristaltic pump or pressure-maintained fluid lines. In other examples, a fluid pump may provide non-uniform fluid flow particularly where the application requires a low fluid volume.

Oval gear meter 100 may be configured to measure fluid flow through system 10 and may include a housing 102 defining a chamber 106, a fluid inlet 104 and a fluid outlet 105. Fluid inlet 104 may be in fluid communication with first fluid line 14 and provides fluid flow from the first fluid line into chamber 106. Oval gears 108 and 110 are installed within chamber 106 and are configured to rotate in concert about fixed axes of rotation 112 and 114, respectively, in response to fluid flow through the chamber. Fluid exits chamber 106 by way of fluid outlet 105 which is in fluid communication with second fluid line 16.

Accordingly, fluid provided by fluid pump 12 flows through fluid line 14 and into oval gear meter through fluid inlet 104. The fluid then flows through oval gear meter 100, wherein the volume of flow is measured, and out oval gear meter 100 through fluid outlet 105 and into second fluid line 16.

Figure 2:
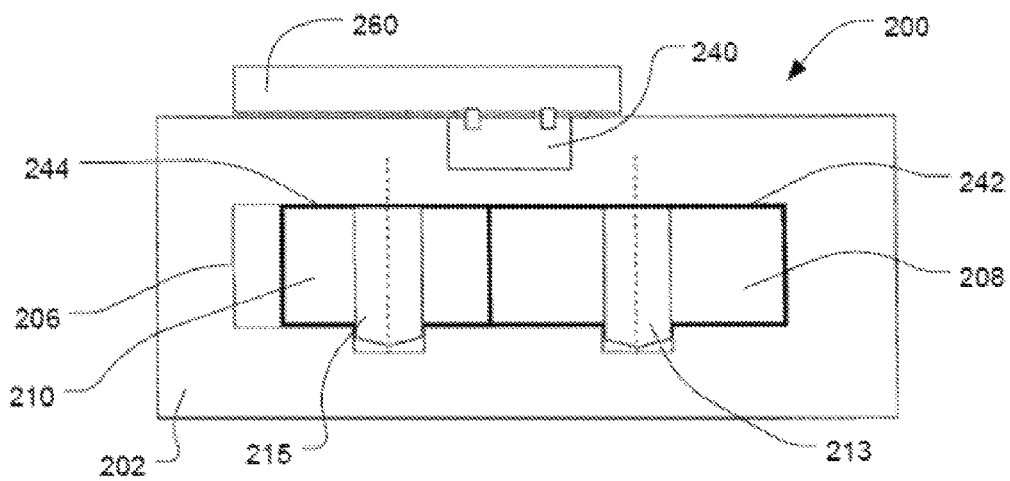
FIG. 2 is a cross-sectional side view of an oval gear meter taken along line A-A of FIG. 1.

FIG. 2 is a cross-sectional side view of an oval gear meter 200 that may be taken along line A-A of the oval gear meter 100 of FIG. 1. Oval gear meter 200 includes a housing 202, oval gears 208 and 210, a non-contact sensor 240 and a controller 260. Oval gears 208 and 210 are installed within a chamber 206 defined by housing 202 and may be configured to rotate about axles 213 and 215, respectively. Housing 202 and oval gears 208 and 210 may comprise any suitable material compatible with the fluid being metered, for example a moldable plastic.

In certain embodiments, oval gear meter 200 may also include non-contact sensor 240 and controller 260. Non-contact sensor 240 may be configured to sense a detectable area (not shown) provided on top surfaces 242 and 244 of oval gears 208 and 210, respectively. For example, non-contact sensor 240 may be a magnetic sensor configured to sense a detectable area comprising a magnet installed on or within at least one of the oval gears. In another example, non-contact sensor 240 may be an optical sensor configured to emit a wavelength onto at least one top surface 242 or 244 of the oval gears including a detectable area and sense a reflectance of the wavelength off at least one of the top surfaces. U.S. Pat. No. 7,523,660, filed Dec. 19, 2007, and U.S. Pat. No. 8,069,719, filed Feb. 11, 2009, provides examples of oval gears incorporating non-contact sensors, the entire disclosure of each is hereby incorporated herein by reference. It can be appreciated that oval gear meter 200 may include any number of non-contact sensors and any number of detectable areas suitable for a particular application of the meter. Non-contact sensor 240 may also be configured to generate a detection signal based on the detection, or lack of detection, of a detectable area.

Oval gear meter 200 may also include controller 260 configured to calculate a volume of fluid flow through the meter based on the detection signal of non-contact sensor 240. The controller may be configured to receive a detection signal of non-contact sensor 240 and determine a rotational count of the oval gears based on the detection signal. The rotational count may be indicative of the number of rotations made by oval gears 208 and 210 in response to fluid flow through chamber 206. As will be discussed further herein, a volume of fluid passing through an oval gear meter may be calculated when the number of rotations (complete and partially complete) made by the oval gears is known and a volume of fluid per rotation is known. Accordingly, controller 260 may be able to measure a volume of fluid passing through the meter by measuring a rotational count of the oval gears.

Figure 3A:
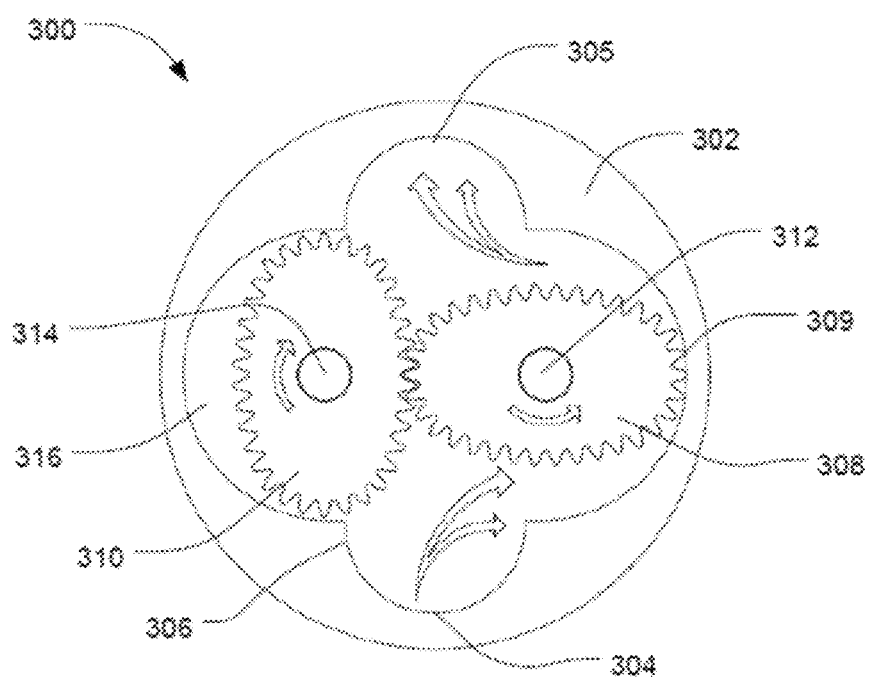
FIGS. 3A and 3B are top plan views illustrating fluid flow through an oval gear meter.
Figure 3B:
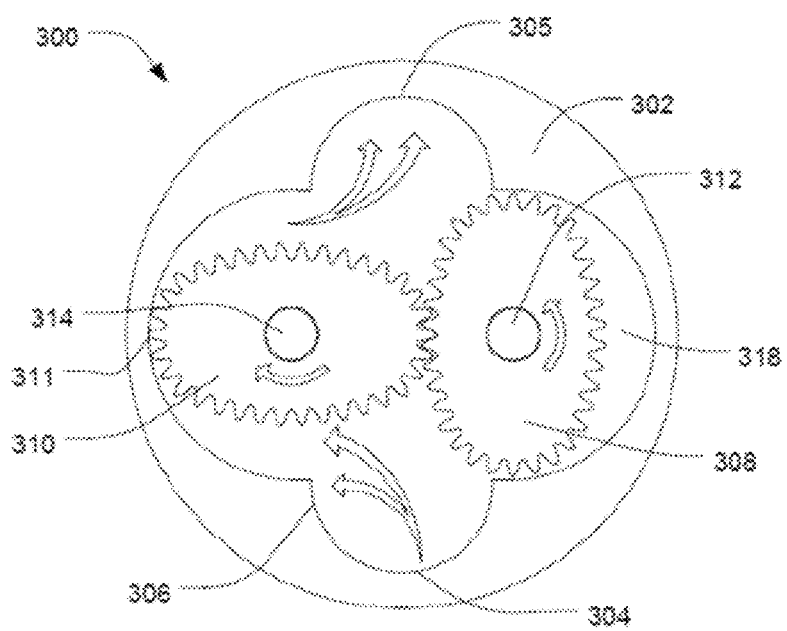

FIGS. 3A and 3B are top plan views illustrating fluid flow through an oval gear meter 300. Oval gear meter 300 includes a housing 302 defining a chamber 306 having fluid inlet 304 and fluid outlet 305. Oval gears 308 and 310 are installed within chamber 306 and are configured to rotate in concert about axes of rotation 312 and 314, respectively, in response to fluid flow through the chamber. Oval gears 308 and 310 are configured to intermesh thereby preventing fluid from fluid inlet 304 to pass between the gears. Accordingly fluid flows around the oval gears by way of fluid pockets 316 and 318.

FIG. 3A shows oval gear meter 300 in a first rotational position where in fluid may be introduced into chamber 306 through fluid inlet 304. As noted above, the intermeshing of oval gears 308 and 310 prevent fluid from passing in between the gears thereby forcing the incoming fluid toward a vertex 309 of oval gear 308 and urging oval gear 308 to rotate in a counter-clockwise direction. The counter-clockwise torque applied across oval gear 308 in turn urges the clockwise rotation of oval gear 310. FIG. 3B shows oval gear meter 300 in a radially advanced rotational position relative to the rotational position shown in FIG. 3A, wherein oval gear 308 has rotated 90 degrees counter-clockwise and oval gear 310 has rotated 90 degrees clockwise. In this rotational position of oval gear meter 300, the rotation of oval gear 308 has formed fluid pocket 318 defined by the surface of oval gear 308 and a wall of chamber 306. Concurrently, fluid from fluid inlet 304 is forced toward a vertex 311 of oval gear 310 thereby urging oval gear 310 to rotate in a clockwise direction. This in turn urges oval gear 308 to continue rotation in a counter-clockwise direction to release the fluid in fluid pocket 318. It can be appreciated that a similar fluid pocket 316 may be formed between oval gear 310 and a wall of chamber 306, as shown in FIG. 3A.

In this example, the volume of fluid flowing through oval gear meter 300 in one full rotation of oval gears 308 and 310 is equivalent to the volume of fluid contained by four fluid pockets. More specifically, one full rotation of the gears causes fluid pockets 316 and 318 to each be released twice. Generally, the volume of the fluid pockets of an oval gear are precisely measured, therefore a volume of fluid flow through the oval gear meter may be calculated by determining a rotational count of the oval gears of the meter. For example, a rotational count may be determined by a controller of oval gear meter 300 that indicates that two full rotations of oval gears 308 and 310 have occurred. Based on this rotational count, it is known that eight fluid pockets have been dispensed by the oval gear meter (e.g., four of fluid pocket 316 and four of fluid pocket 318) and thus a volume of fluid may be calculated if the volume of the fluid pockets are known.

In various embodiments, a rotational count need not correspond with a full or complete rotation of the oval gears of an oval gear meter. In some examples, each rotational count may correspond with a known, partial rotation of the oval gears. In other examples, each rotational count may correspond with a full rotation, but the rotational count may be fractionally incremented by a known, fractional amount. Furthermore, oval gear meters may be configured to increase the resolution of measurement thereby allowing a more precise measurement of fluid flow through the meter. These configurations may be useful, for example, in low fluid flow applications. Exemplary embodiments describing such configurations can are described further in U.S. patent application Ser. No. 13/833,582 filed on Mar. 15, 2013, the entire disclosure of which is hereby incorporated herein by reference.

Figure 4A:
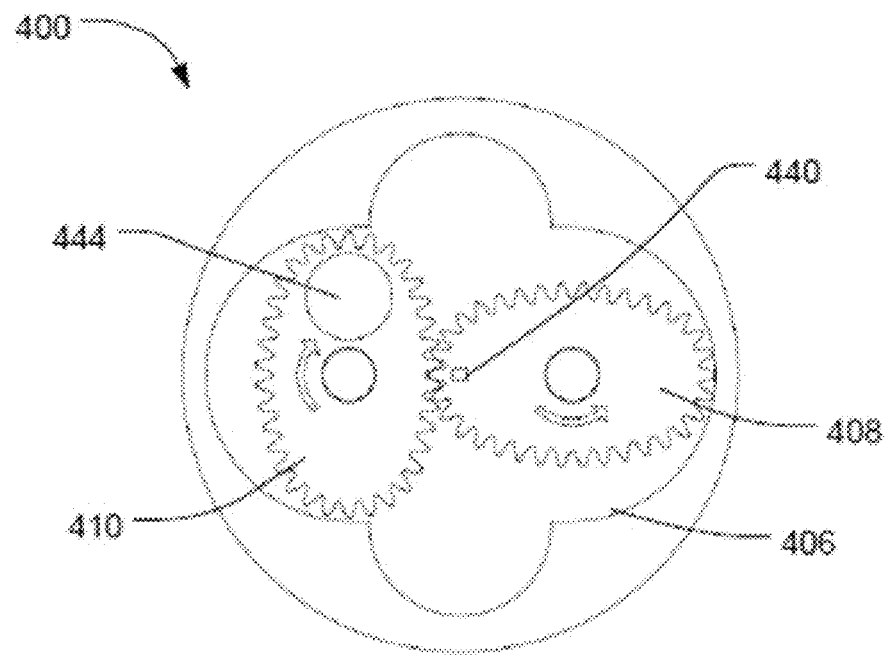
FIG. 4A is a top plan view of an oval gear meter including a non-contact sensor and a detectable area.

FIG. 4A is a top plan view of an exemplary oval gear meter 400 including a non-contact sensor 440 and a detectable area 444 according to some embodiments of the invention. Non-contact sensor 440 may be configured to sense detectable area 444 provided on a surface of oval gear 410 and generate a detection signal. Non-contact sensor 440 may be mounted in a housing (not shown) of oval gear meter 400 positioned above the top surfaces 242, 244 of oval gears 408 and 410. As indicated in FIG. 4A oval gear meters 408 and 410 are configured to rotate counter-clockwise and clockwise, respectively, in response to fluid flow through chamber 406. The rotation of oval gear 410 causes detectable area 444 to pass through a sensing region of non-contact sensor 440 that may be located underneath the sensor. Upon sensing detectable area 444, non-contact sensor may generate a detection signal. Thus, a detection signal of non-contact sensor 440 may be indicative of a rotational position of oval gears 408 and 410 wherein detectable area 444 is underneath non-contact sensor 440. It should be noted that relative terms such as "above," "top" surface, and "underneath" as used herein are intended to provide clarity and orientation with respect to the drawings, and does not limit devices or systems herein described to any particular orientation.

In this example, non-contact sensor may be configured to generate a "positive" signal (hereinafter also referred to as "1" or "high") when the sensor senses the detectable area and a "negative" signal (hereinafter also referred to as "0" or "low") when the sensor does not sense the detectable area. It can be appreciated that the detection signal generated by a non-contact sensor may be of any form in any format suitable for indicating a sensing of a detectable area. In certain examples, a non-contact sensor may be configured to not generate a detection signal when a detectable area is not sensed. In such an example, the lack of a signal may still be indicative of a rotational position wherein the detectable area is not within a sensing region of the sensor.

Oval gear meter 400 may also include a controller configured to calculate a rotational count based on the detection signal provided by non-contact sensor 440. In this example, oval gear meter 400 is configured such that one full rotation of oval gears 408 and 410 causes non-contact sensor 440 to sense detectable area 444 only once. Thus, a rotational count may be determined based on the number of times a detectable area is sensed by the non-contact sensor. It will be appreciated that in some embodiments, any number of detectable areas can be employed on one or both oval gears 408 and 410 to detect any suitable fraction of full rotations.

Figure 4B:
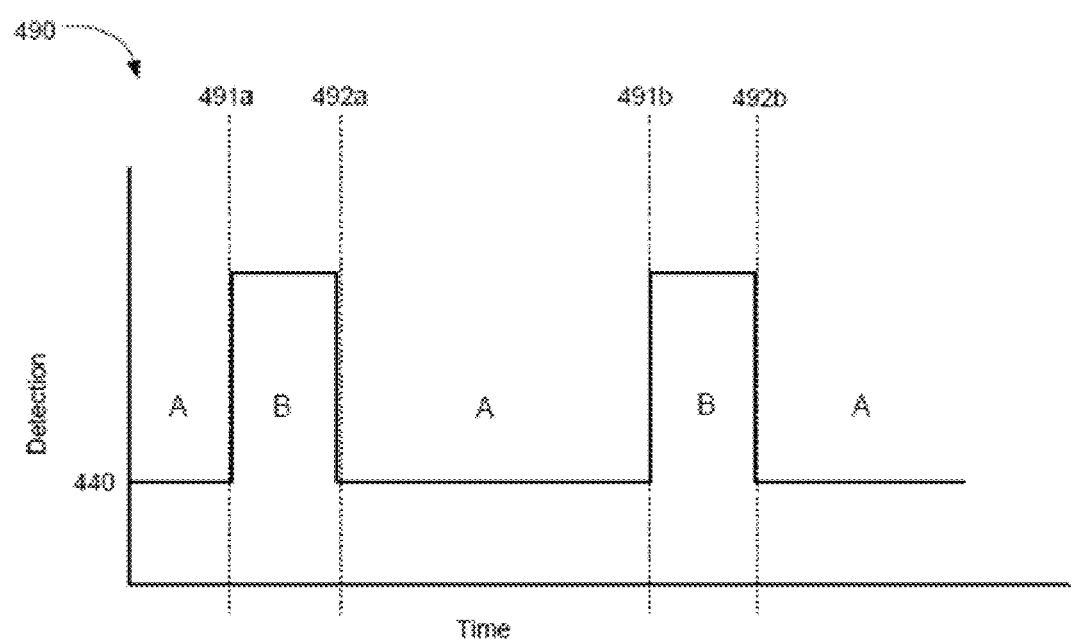
FIG. 4B is a plot of a detection signal of a non-contact sensor of the oval gear meter of FIG. 4A over time.

FIG. 4B is a plot 490 of a detection signal of non-contact sensor 440 of oval gear meter 400 over time. More specifically, plot 490 shows the detection signal of non-contact sensor 440 sensing detectable area 444 as oval gears 408 and 410 rotate in a forward direction in response to fluid flow through the meter. Plot 490 includes time points 491a, 491b, 492a and 492b. Initially, the detection signal of non-contact sensor 440 is low indicating that oval gears 408 and 410 are in a rotational position wherein the detectable area is not within a sensing region of the sensor. The detection signal is high between time points 491a and 492a, and also 491b and 492b, and is indicative of rotational positions of the oval gears wherein the detectable area is sensed by non-contact sensor 440. The detection signal becomes low again between time points 492a and 491b, and also after time point 492b, and is indicative of rotational positions of the oval gears wherein the detectable area is not sensed by the sensor. The time period between time points 491a and 491b, or alternatively, 492a and 492b, may represent all the rotational positions in one full rotation of oval gears 408 and 410 as there is only one detectable area 444 in oval gear meter 400.

In this example, the rotational positions of the oval gears in one full rotation of oval gear meter 400 may be categorized into rotation states A and B. Rotation state A comprises all the rotational positions wherein detectable area 444 is not sensed by non-contact sensor 440 and is shown in plot 490 before time point 491a, between time points 492a and 491b, and also after time point 492b. Rotation state B comprises all the rotational positions wherein the detectable area is sensed by the non-contact sensor and is shown in plot 490 between time points 491a and 492a, as well as 491b and 492b. When non-contact sensor 440 senses rotation state A and B, it generates a negative and positive detection signal, respectively.

Figure 4C:
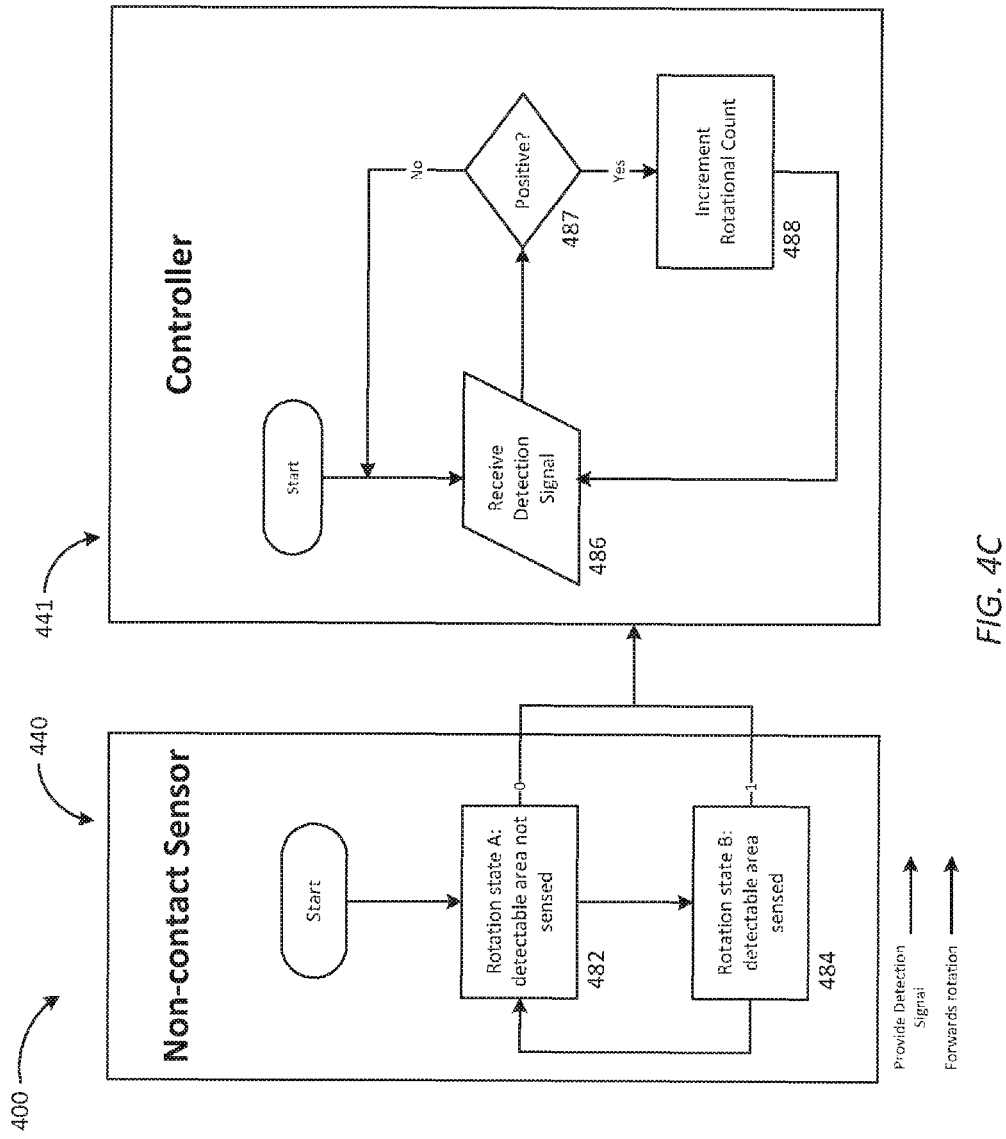
FIG. 4C is a flow diagram illustrating a method for determining a volume of fluid flow through the oval gear meter of FIG. 4A.

Oval gear meter 400 may also include a controller configured to calculate a volume of fluid flow through the meter by determining a rotational count based on the detection signals provided by non-contact sensor 440. FIG. 4C is a flow diagram illustrating a method for determining a volume of fluid flow through oval gear meter 400 in response to fluid flow through the meter. Initially, non-contact sensor 440 may sense in step 482 rotation state A indicative of a rotational position of the oval gears wherein the detectable area is not within a sensing region of the sensor. As oval gears 408 and 410 rotate in a forward direction in response to fluid flow through the meter, the gears eventually reach a rotational position wherein detectable area 444 is within a sensing region of the non-contact sensor. Accordingly, non-contact sensor may sense rotation state B in step 484. It can be appreciated as the oval gears continue to rotate in oval gear meter 400, non-contact sensor 440 senses a sequence of rotation states comprising rotation state A and B, in order. As noted above, non-contact sensor 440 may be configured to generate a negative detection signal and a positive detection signal when rotation state A and B are sensed, respectively, and provide the signals to controller 441, shown in FIG. 4C as a dashed line.

Concurrently, controller 441 of oval gear meter 400 is configured to receive the detection signal from non-contact sensor 440 and determine a rotational count. The controller is initially in a state of receiving 486 wherein the controller is configured to receive a detection signal from the non-contact sensor. Upon receiving a detection signal indicative of both a rotation state and a rotational position of oval gears 408 and 410, the controller determines in step 487 whether the detection signal is positive. If the detection signal is positive then the controller increments the rotational count 488 and returns back to receiving state 486. If the detection signal is negative, then the controller returns back to receiving state 486 without incrementing the rotational count. Referring back to FIG. 4B, it can be appreciated that a rotational count of oval gear meter may be incremented by controller 441 at time points 491a and 491b when the detection signal goes from low to high. It can be appreciated that the method of FIG. 4C may alternatively be configured to increment a rotational count when the detection signal goes from high to low (e.g., at time points 492a and 492b) by modifying step 487 to check to see if the detection signal is negative. In this example, because non-contact sensor 440 senses the detectable area 444 only once during each rotation, every increment of rotational count in step 488 corresponds with one full rotation of the oval gears. It can be appreciated that a volume of fluid flow through oval gear meter 400 may be determined using the rotational count and a known volume of fluid pockets of the meter.

As noted above, oval gear meters including non-contact sensors tend to measure fluid volume accurately in applications having a high fluid flow rate or a relatively uniform fluid flow (e.g., fluid provided by peristaltic pumps or from pressure-maintained fluid lines). In these applications, the uniformity of flow tends to provide for continuous rotation of the oval gears in a forward direction, which is conducive to an accurate measurement of fluid flow. In applications having low fluid flow rates or where the fluid flow is non-uniform, oval gear meters including non-contact sensors may have a lower accuracy of measurement. These applications tend to provide an irregular flow rate thereby causing non-continuous rotation of the oval gears, which may include a backwards rotation of the oval gears. For example, non-uniform flow generated by a diaphragm pump may cause pressure shocks which generate fluid oscillations in the fluid lines after each pump cycle. The fluid oscillations may produce vibrations, or "jitter," of the oval gears or backflow of fluid into the oval gear meter from the fluid outlet. Jitter or backflow of fluid occurring when the oval gears are in a rotational position wherein the detectable area is near a sensing region of the non-contact sensor may induce false detection signals from the sensor which may cause a controller to generate an inaccurate rotational count. Accordingly, the controller may calculate an inaccurate volume of fluid flow through the oval gear meter based on the inaccurate rotational count.

Figures 5A, 5B:
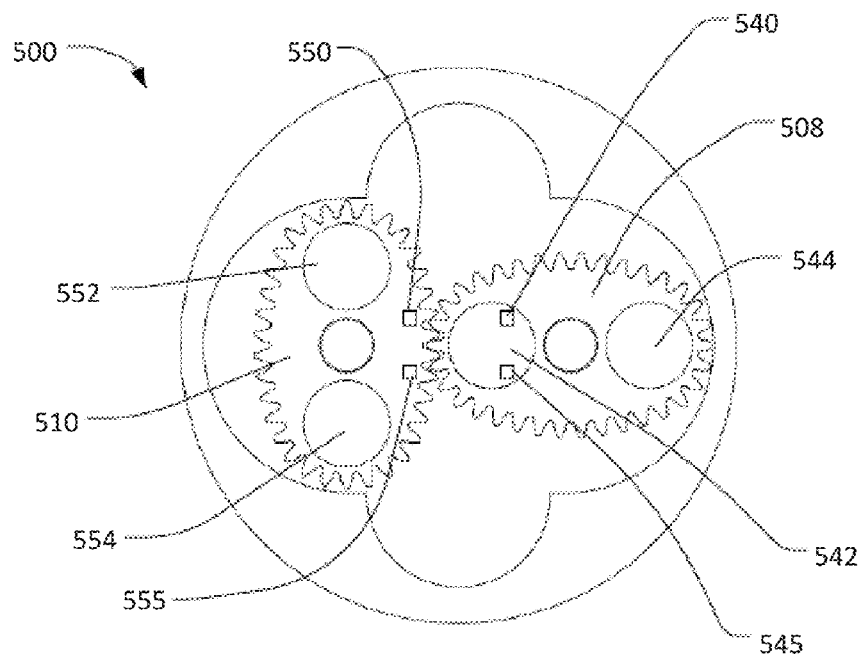
FIG. 5A is a top plan view of an oval gear meter including four detectable areas and four non-contact sensors.
FIG. 5B is a table showing the rotation states of the oval gear meter of FIG. 5A.

FIG. 5A is a top plan view of an oval gear meter 500 including four detectable areas and four non-contact sensors. Oval gear meter 500 includes oval gear 508 having detectable areas 542 and 544, oval gear 510 having detectable areas 552 and 554, and non-contact sensors 540, 545, 550 and 555. Non-contact sensors 540 and 545 are positioned linearly along a rotational path oval gear 508 such that both detectable areas 542 and 544 pass through a sensing region of each sensor. As shown in FIG. 5A, non-contact sensors 550, 555, oval gear 510 and detectable areas 552 and 554 are disposed in a similar configuration.

The configuration of oval gear meter 500 provides for the rotational positions in one full rotation of oval gears 508 and 510 to be divided into eight rotation states A through H. FIG.

5B is a table 560 showing each rotation state and the corresponding detection signals from each non-contact sensor. In this example, oval gear meter 500 is configured such that cycling through the sequence of rotation states A through H once corresponds with a half rotation of oval gears 508 and 510. For example, the non-contact sensors may sense rotation states A through D as detectable area 542 passes through the sensing regions of non-contact sensors 540 and 545. As the oval gears continue to rotate in a forward direction, rotation states E through H may be sensed by the non-contact sensors as detectable area 552 passes through the sensing regions of non-contact sensors 550 and 555. Upon reaching rotation state H, it can be appreciated that the oval gears have completed half a rotation as only two of the four detectable areas have been sensed. The sequence of rotation states A through H may be repeated with regard to detectable areas 544 and 554.

Oval gear meter 500 may include a controller configured to advance through the sequence of rotation states A through H and calculate a volume of fluid flow through the meter. For example, the non-contact sensors may be configured to collectively detect rotation states A through H indicative of a rotational position of oval gears 508 and 510 and each generate and provide a detection signal to the controller of the meter. The controller may be configured to receive detection signals from the four non-contact sensors, advance through the sequence of rotation states A through H, and increment a rotational count upon reaching an end of the sequence. In one example, the controller may be configured to increment the rotational count fractionally when the end of the sequence is reached, for example by 0.5, to reflect that one cycle through the sequence of rotation states A through H of oval gear meter 500 is indicative a half rotation of oval gears 508 and 510. In another example, the measurement resolution of the oval gear meter may be increased by configuring the controller to increment the rotational count twice, once after rotation state D is reached, and once again after rotation state H is reached, wherein each increment of the rotational count corresponds to a quarter rotation of the oval gear indicative of the volume of one fluid pocket of oval gear meter 500.

As noted above, another cause of measurement error in an oval gear meter may be the leakage of fluid around the oval gears of the meter. Referencing FIG. 3A, generally, an oval gear meter may include a housing 302 defining a chamber 306 and two oval gears 308 and 310 that are configured to rotate in response to fluid flow through the meter. The housing comprise include one or more sidewalls further defining the chamber 306. Each oval gear may include teeth that are configured to intermesh as to not allow fluid to pass between the gears. Accordingly, fluid entering the meter through fluid inlet 304 may be forced toward the wall of the chamber and a vertex 309 and 311 of each respective oval gear which urges the rotation of the oval gears. Each oval gear is generally configured so that there is gap between the wall of the chamber and a tooth at the vertex of each oval gear. The cap is appropriately small to minimize leakage between the oval gear and the chamber wall, but appropriately large as to allow the oval gears to prevent the tooth from scraping against the wall thereby impeding the rotation of the gear. Applicants have found that oval gear meters in low flow applications may have increased measurement error due to leakage of fluid through this gap between the gear and the chamber wall when compared to applications with a higher fluid flow.

Flow meters such as those herein described can be incorporated into fluid systems. For example, in some instances, a meter can be used to measure an amount of product added to a fluid for performing a process, or added directly to the process itself. Such meters can help ensure that an appropriate amount of product has been added for the process. It will be appreciated that many processes utilizing a metered product are known. In some exemplary applications, sanitizers or cleaners can be added to water to create a solution for a clean-in-place (CIP) process.

Some flow meters, such as the oval gear meters herein described, comprise at least one rotating element configured to rotate as fluid flows therethrough. As described, in some cases, the metered volume of fluid that travels through the meter corresponds to, for example, the number of revolutions of the rotating elements. However, in some cases, when a product flowing through a meter runs out (e.g., a reservoir from which the product is being pumped becomes empty), air flowing through the meter will continue to cause the rotating element of the meter to continue rotating. That is, in some embodiments, the rotating element is nonselective as to the fluid flowing therethrough, but rather simply detects the rotation of the rotating element. In such an instance, the rotating element will continue to detect fluid (i.e., air) flowing therethrough but will be unable to differentiate the flowing air from the product. Thus, the flow meter may provide an inaccurate measure of the amount of product that has flowed therethrough. The addition of air instead of product can lead to a variety of negative consequences, such as damaging equipment suited for receiving the product or rendering the resulting fluid unsuitable for performing a desired process. For example, in some CIP processes, a resulting process fluid may have too low of a concentration of a product for adequately performing a cleaning or sanitizing process.

Accordingly, various embodiments of flow meters can include an out of product (OOP) sensor incorporated for detecting an OOP event. In some embodiments, an OOP sensor can include a capacitive sensor. A capacitive sensor can include a first electrode and a second electrode electrically insulated from the first. In some embodiments, the capacitive sensor can include an insulator separating the first and second electrodes. During use, an electrical potential can be applied between the first and second electrodes of the capacitive sensor to effect an electric field therebetween.

The first and second electrode can be positioned such that the electric field between the electrodes permeates at least a portion of the fluid path within the flow meter. That is, fluid flowing through the flow meter experiences the electric field effected by the potential difference between the first and second electrodes. Thus, anything in the fluid path during in the area of the electric field will act as a dielectric and affect a measure of the capacitance between the two electrodes. Various fluids can be distinguished from others by their dielectric properties which are manifested in a measurement of the capacitance between the two electrodes. For example, a capacitance measurement can be used to distinguish between the presence and absence (i.e., air) of a product flowing through the meter from a product reservoir. In another example, the presence of water contamination in a product can be distinguished from the product free from water contamination. For example, oil or gasoline can be evaluated to detect the presence of water contamination. Various examples are possible in which a change in the dielectric properties representative of a change in the fluid flowing through the flow meter can be detected by measuring the capacitance between the first and second electrodes.

In some embodiments, the first and second electrodes can be susceptible to several errors inside the flow meter housing. For example, an electrically conductive fluid flowing through the flow meter can short electrodes inside the housing, interfering with the capacitance measurement. Additionally, a fluid flowing through the sample might be corrosive or otherwise damaging to the electrodes during the course of use. Accordingly, in some embodiments, the first and second electrodes can be positioned outside of the flow meter housing. The electrodes can be positioned outside the housing proximate a sidewall so that the electric field therebetween still encounters the inside of the housing.

Figure 6:
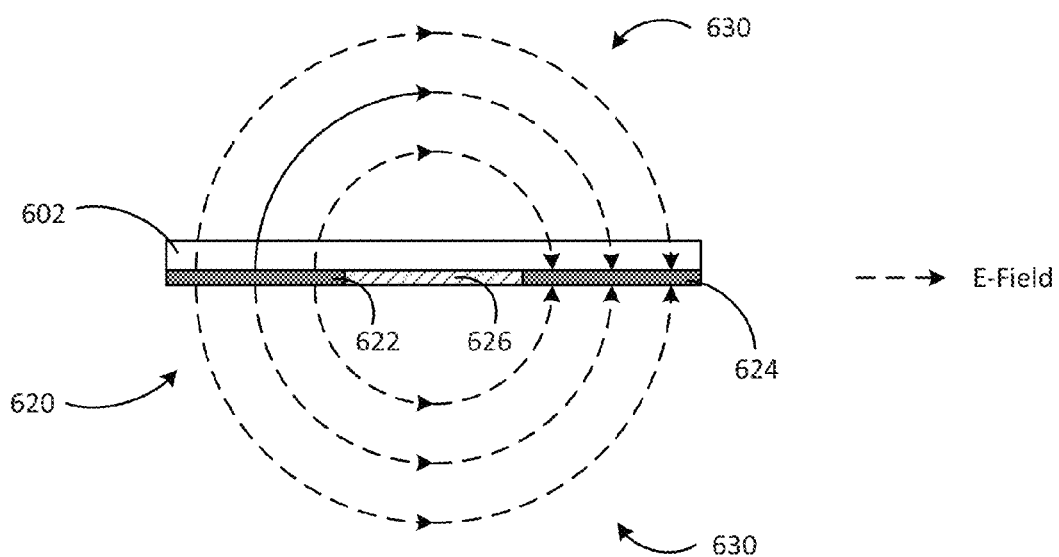
FIG. 6 is a cross-sectional diagram of a housing sidewall proximate a capacitive sensor according to some embodiments of the present invention.

In some examples, the first and second electrodes can be substantially planar and parallel to the housing sidewall to produce a large electric field inside of the housing. FIG. 6 is a cross-sectional diagram of a housing sidewall proximate a capacitive sensor according to some embodiments of the present invention. FIG. 6 shows a capacitive sensor 620 having a first electrode 622, a second electrode 624 and an insulator 626. The capacitive sensor 620 is positioned proximate a housing sidewall 602 of flow meter. In the exemplary diagram, electric field lines 630 extend from the first electrode 622 to the second electrode 624, some of which extend through the sidewall 602 and into the chamber. As shown, in some embodiments, the capacitive sensor is positioned flush against the sidewall 602 to maximize the amount of electric field present in the flow path of the flow meter.

Figure 7:
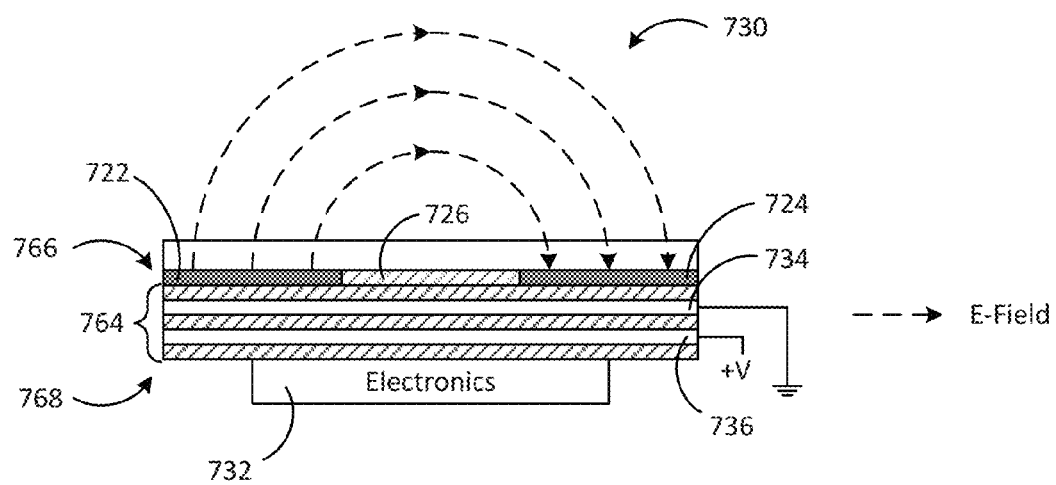
FIG. 7 is a cross-sectional diagram of a capacitive sensor similar to that in FIG. 6 and a capacitive sensor board.

In some embodiments, the capacitive sensor can be positioned on a capacitive sensor board adjacent to a housing sidewall of the flow meter. In some such embodiments, the capacitive sensor board can become an integrated part of the flow meter. FIG. 7 is a cross-sectional diagram of a capacitive sensor similar to that in FIG. 6 and a capacitive sensor board. In the illustrated embodiment of FIG. 7, a capacitive sensor board 764 comprises a first side 766 and a second side 768, opposite the first. The first side 766 can include the first electrode 722, the second electrode 724, and an insulator 726. The second side of the board 764 can include electronics 732 for interfacing with the non-contact sensor of a flow meter (e.g., oval gear meter) and/or the capacitive sensor elements (e.g., the first electrode 722 and/or the second electrode 724). In some embodiments, the capacitive sensor board 764 comprises a ground layer 734 and/or a power layer 736 between the first side 766 and the second side 768 of the board 764. The illustrated capacitive sensor board 764 includes additional insulating layers to electrically insulate the ground layer 734 from the power layer 736 as well as from the first electrode 722, second electrode 724, and electronics 732. As shown in FIG. 7, the ground 734 and power 736 layers act to shield the second side 768 from the first side 766 of the board 764. Accordingly, the electric field lines 730 between the first electrode 722 and the second electrode 724 extend into an internal part of the flow meter on the first side 766 of the board, but because of the shielding of the ground layer 734, do not extend through to the second side 768 and do not interfere with the electronics 732. Similarly, any time-varying signals and other effects from the electronics 732 will not affect the capacitance between the first 722 and second 724 electrodes.

Ground 734 and power 736 layers can further be coupled to electronics 732 to power various electronic components. For example, electronics 732 can comprise a controller and/or other circuitry for controlling a non-contact sensor associated with the flow meter and/or the capacitive sensor. Controller or circuitry can be powered by the power layer 736 and can define a reference via the ground layer. In some embodiments, it can be advantageous to minimize the length of the conductive paths between electrodes and electronics to reduce possible interfering capacitive effects from the conductive paths. Accordingly, in some embodiments, the capacitive sensor board 764 comprises traces, or electrically conductive paths, therethrough for electrically coupling various components on the board 764.

Figure 8A:
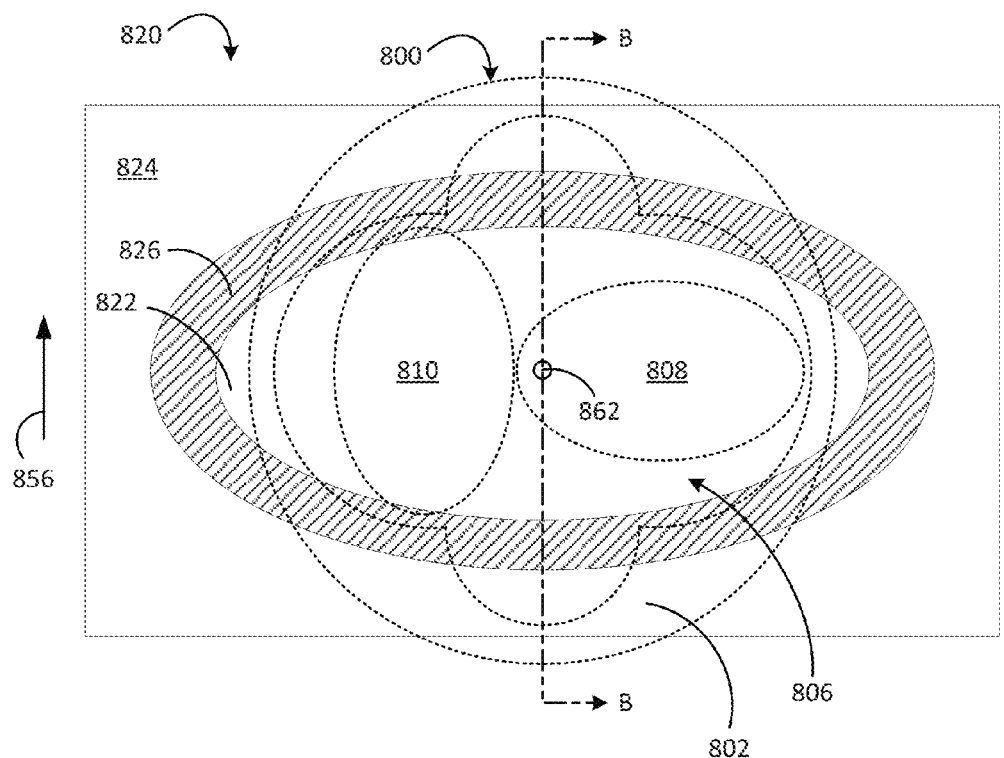
FIG. 8A is a plan view of an exemplary capacitive sensor arrangement having large area electrodes.

In some configurations, the capacitive sensor is configured such that first and second electrodes have a maximum surface area to increase the sensitivity of the capacitive sensor. For example, in some embodiments, the capacitive sensor utilizes substantially the entire capacitive sensor board. FIG. 8A is a plan view of an exemplary capacitive sensor arrangement having large area electrodes. FIG. 8A shows a capacitive sensor 820 comprising a first electrode 822, a second electrode 824, and an insulator 826 separating the first electrode 822 and the second electrode 824 electrodes. It should be appreciated that the illustrated capacitive sensor 820 of FIG. 8A is exemplary, and that a similarly functioning sensor could be designed having different shape, layout or dimension. A large-area capacitive sensor 820 such as that shown in FIG. 8A can increase the sensitivity to the capacitive sensor and make it easier to detect changes in the capacitance due to changes of the fluid flowing through the flow meter. In some embodiments, capacitive sensor 820 can be disposed on a capacitive sensor board such as that shown in FIG. 7. As mentioned, in some embodiments, the electrodes 822, 824 and the insulator 826 can fill substantially an entire side of a capacitive sensor board.

FIG. 8A further illustrates an exemplary arrangement of a capacitive sensor 820 in relation to an oval gear flow meter 800 such as those described previously. In the illustrated example, the large-area capacitive sensor 820 is positioned proximate the chamber 806 of the oval gear flow meter 800 through which fluid flows. Chamber 806 houses oval gears 808 and 810, which are configured to rotate as fluid flows through the meter as described elsewhere herein. Thus, as the fluid flows through the chamber 806, the fluid flows past the first electrode 822 and the second electrode 824 of the capacitive sensor 820.

Figure 8B:
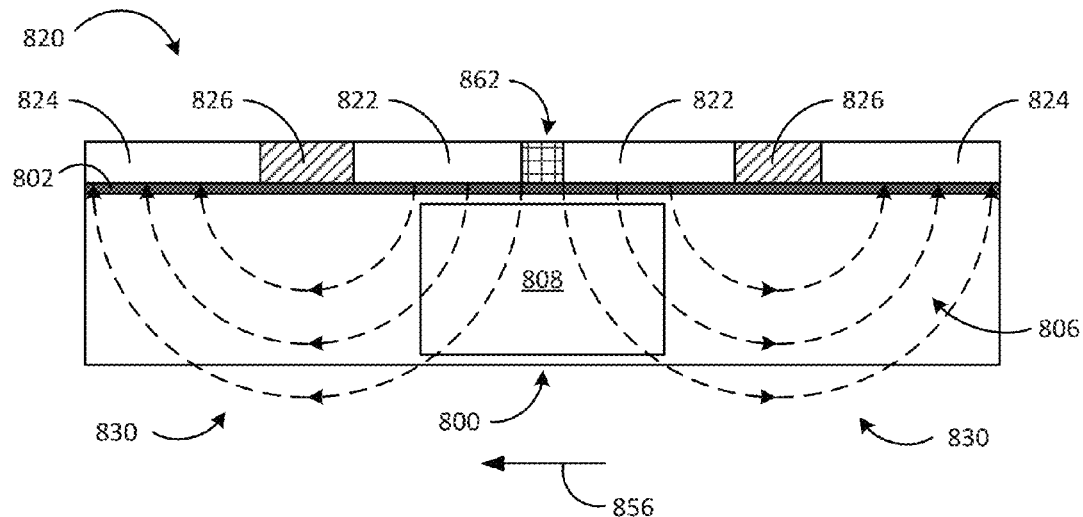
FIG. 8B is a cross sectional view of the capacitive sensor and flow meter of FIG. 8A, taken along line B-B.

FIG. 8B is a cross sectional view of the capacitive sensor and flow meter of FIG. 8A, taken along line B-B. FIG. 8B shows a capacitive sensor 820 comprising a first electrode 822 and a second electrode 824. The capacitive sensor 820 is positioned proximate a housing 802 of an oval gear flow meter 800. The housing 802 defines a chamber 806 comprising an oval gear 808 disposed therein. As described elsewhere herein and shown, a system can be arranges to that fluid generally flows through the flow meter 800 in the direction of arrow 856. FIG. 8B illustrates exemplary electric field lines 830 extending between the first electrode 822 and the second electrode 824. As can be seen, the electric field extends into the housing through which fluid flows and encounters the oval gear 808. Accordingly, when an electrical potential is applied between the first electrode 822 and the second electrode 824 and a fluid is flowing through the chamber 806, the fluid will flow through the electric field of the capacitive sensor 820 and act as a dielectric affecting a capacitance measurement between the first electrode 822 and the second electrode 824.

During operation, a fluid flows through the flow meter and its volume is measured. While fluid is flowing, the capacitance between the first and second electrodes of the capacitance sensor is monitored over time. A change in the capacitance could indicate a change in the dielectric properties of the fluid flowing through the flow meter, potentially indicating an OOP event. In some embodiments, capacitive sensor is coupled to a controller configured to control an electrical potential applied across first and second electrodes and to measure the capacitance therebetween. The controller can be configured to measure the capacitance over time, and detect an OOP event based on the measured capacitance. In some embodiments, the controller is configured to detect an OOP event when the capacitance crosses above or below a predetermined threshold. In alternative configurations, the controller can detect an OOP event based on a relative change in the capacitance. Various indicators of an OOP event based on the capacitance measurement can be defined by a user, or can be selected by the user from a predetermined list. In various embodiments, the controller can be configured to alert a user or system operator of an OOP event. The alert can comprise a visual alert, an auditory alert, or both. In some configurations, the controller can generate a report indicating an OOP event was detected.

While performing a capacitance measurement, it is possible that factors other than a change in fluid properties can affect the measured capacitance. For example, a local change in temperature can effect a change in the measured capacitance. In such instances, such a change in capacitance could result in a false OOP event detection. Thus, it is desirable to determine capacitive changes due specifically to a change in the fluid flowing through the flow meter.

In some embodiments, the capacitive sensor comprises a first capacitor comprising the first and second electrodes and a reference capacitor comprising third and fourth electrodes. The reference capacitor can be positioned proximate the first capacitor and such that an electric field between the third and fourth electrodes does not permeate a portion of the fluid flow path through the flow meter. Thus, the capacitance measured between the third and fourth electrodes of the reference capacitor does not depend on the dielectric properties of the fluid flowing through the flow meter. However, if the reference capacitor is placed proximate the first capacitor, the capacitance measured between the third and fourth electrodes should be affected by external factors similarly to the capacitance between the first and second electrodes. Accordingly, a comparison of the first and second capacitances can help eliminate false OOP event detections.

Figure 9:
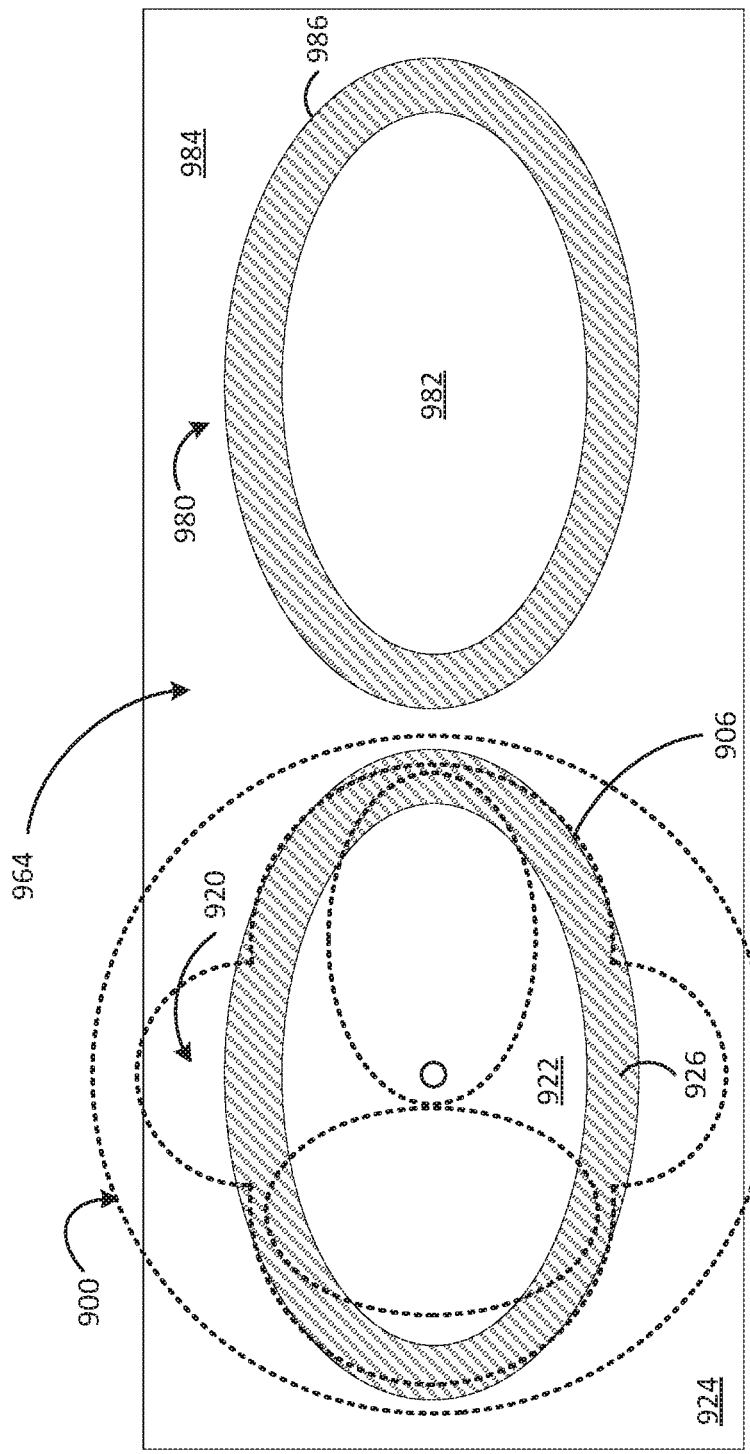
FIG. 9 is a plan view of one possible configuration of a capacitive sensor board.

In some configurations, the reference capacitor can be disposed, for example, on a capacitive sensor board along with the first capacitor. FIG. 9 is a plan view of one possible configuration of a capacitive sensor board. In the embodiment of FIG. 9, the capacitive sensor board 964 comprises a first capacitor 920 comprising a first electrode 922 and a second electrode 924, and a reference capacitor 980 comprising a third electrode 982 and a fourth electrode 984. The first electrode 922 and second electrode 924 are separated by a first insulator 926, and the third electrode 982 and fourth electrode 984 are separated by a second insulator 986. In the illustrated embodiment, the second electrode 924 of the first capacitor 920 and the fourth electrode 984 of the reference capacitor 980 are electrically coupled. However, in some configurations, the second electrode 924 and the fourth electrode 984 are electrically insulated from one another.

During an exemplary operation, the capacitive sensor board 964 of FIG. 9 is disposed proximate the chamber of a flow meter through which fluid flows. The capacitive sensor board can be positioned such that only the first capacitor 920 is adjacent to the chamber 906 of the flow meter 900, while the reference capacitor 980 is not. In such a configuration, the flow path of fluid through the flow meter 900 travels through the an electric field created by a potential difference between the first electrode 922 and the second electrode 924 of the first capacitor 920, but does not encounter an electric field created by the third electrode 982 and the fourth electrode 984 of the reference capacitor 980. Equivalently, the fluid flowing through the flow meter will act as a dielectric between the electrodes of the first capacitor 920, but not between the electrodes of the reference capacitor 980. In such a configuration, the first capacitor 920 and the reference capacitor 980 are in a similar environment, and so should experience similar changes in capacitance due to temperature variations and the like. However, changes in the dielectric properties of fluid between the electrodes can impact individual capacitances.

As fluid is flowing through the sample, a controller or the like can determine the amount of fluid (e.g., flow rate, volume, etc.) flowing through the flow meter based on non-contact sensor. The controller or the like can simultaneously measure the capacitance of the first capacitor and the reference capacitor and compare the two. A detected change in the first capacitance that is not present in the second capacitance can indicate a change in the fluid flowing through the flow meter, for example, an OOP event has occurred. In some embodiments, the detected change must meet a predetermined criterion or set of criteria, such as crossing a threshold, changing by a certain amount or percentage, and/or changing in a predetermined direction. In various embodiments, the controller or the like can alert a system operator of the detected possible OOP event as described elsewhere herein.

In an alternative embodiment, the capacitor board can include a first capacitor such as that shown in FIG. 8A positioned on a first side of the capacitive sensor board and a reference capacitor similar to the first positioned on the second side of the capacitive sensor board. That is, the first capacitor and the reference capacitor can be disposed on opposite sides of the capacitive sensor board. In some such embodiments, the capacitive sensor board comprises ground and power layers as illustrated in FIG. 7 in order to electrically isolate the first capacitor from the reference capacitor. In some systems comprising a capacitive sensor board having large area first and reference capacitors on opposite sides of the board, electronics such as a controller can be positioned on a separate board, such as a control board, for example.

According to some embodiments, other methods can be performed in addition to or instead of measuring the capacitance of a reference capacitor to distinguish capacitance changes due to a change in the fluid flowing through the flow meter. In some instances, for example, changes in a measured capacitance due to temperature or other external factors can be gradual compared to a change in capacitance due to a change in the dielectric properties of material in the electric field between the capacitive electrodes.

Figure 10:
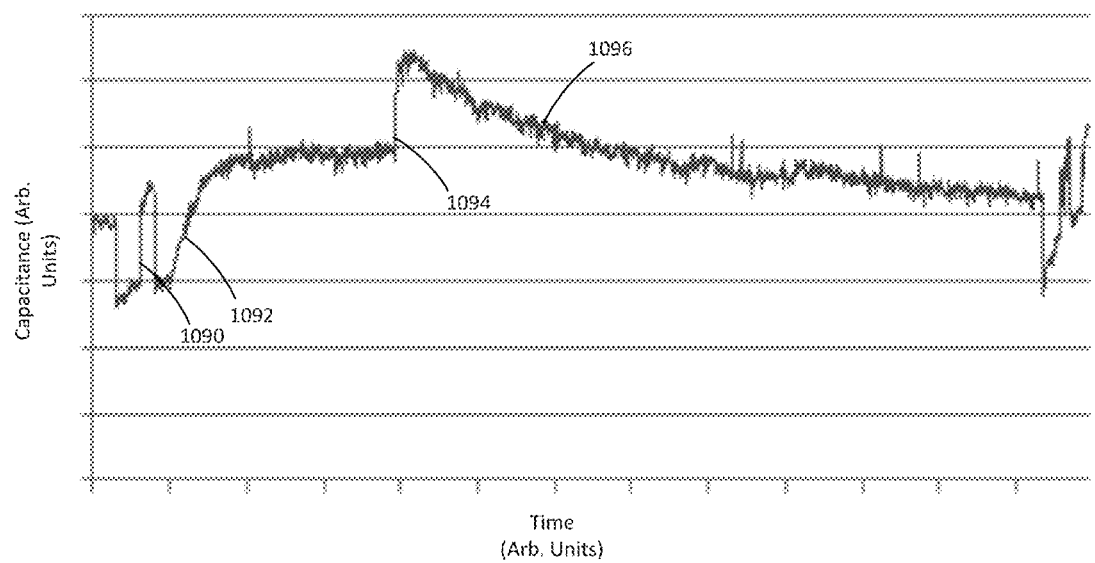
FIG. 10 is an exemplary plot of capacitance vs. time as measured by a capacitance sensor during a fluid flow processes.

FIG. 10 is an exemplary plot of capacitance vs. time as measured by a capacitance sensor during a fluid flow processes. As shown, the capacitance varies over time. In some instances, such as at 1090 and 1096, the capacitance sharply increases, whereas at other times (e.g., 1092, 1094), change is gradual. In other words, the time derivative at times 1090 and 1096 is significantly larger in magnitude than it is at times 1092 or 1094. Accordingly, OOP event detection can be performed by analyzing the time derivative of the capacitance signal, and no reference capacitance measurement is necessary.

In some embodiments, the controller is configured to measure the capacitance over time and to determine the temporal derivative of the capacitance signal. The controller can compare the derivative to a threshold and, if the derivative crosses the threshold, the controller can signal the occurrence of an OOP event. In some configurations, an OOP event is considered to have occurred only if the derivative of the capacitance meets a predetermined criterion or set of criteria, such as exceeding a threshold. In other embodiments, the absolute value of the derivative of the capacitance can be compared to a threshold for determining the occurrence of an OOP event. In some embodiments, the derivative analysis technique of OOP event detection can performed using systems including a single large area capacitive sensor such as in FIG. 8A on one side of a capacitive board and electronics on the other, such as illustrated by FIG. 7. Of course, other configurations are possible in which electronics and the capacitive sensor are not on the capacitive sensor board.

As described, a non-contact sensor can be utilized to monitor the rotation of the rotating element to determine the flow rate and/or volume of fluid flowing through the meter. In some embodiments, the non-contact sensor can be controlled by a controller or other components mounted on the capacitive sensor board. Accordingly, the non-contact sensor can be positioned proximate the capacitive sensor. In some embodiments, the non-contact sensor comprises an optical assembly which can be used simultaneously as the capacitive sensor. In some examples, the non-contact sensor can include an optical emitter for emitting light of at least a first wavelength and an optical detector for receiving light of at least the first wavelength.

An optical assembly can be positioned outside of the housing and emit light into the housing and detect light from within the housing. Accordingly, the housing can include at least a portion that is transparent to at least the first wavelength of light to allow for optical communication between the optical assembly and the detectable areas inside the housing. In some embodiments, one or more entire sidewalls of the housing can be transparent to at least the first wavelength of light. For example, a sidewall can comprise a transparent material such as sapphire for the transmission of light therethrough.

The thickness of the portion of the housing through which light is emitted and detected can be specified for the intended application of the flow meter. In some embodiments, a sidewall of the housing can be between 2 and 4 mm thick to provide high strength for the housing. In some examples, such a housing can withstand up to 150 psi internal pressure. In other embodiments, the thickness of the housing sidewall can be approximately 0.5 mm thick or less to increase sensitivity of measurements being performed through the sidewall (e.g., optical or capacitive measurements).

The optical assembly can be configured so that the optical emitter emits light into a portion of the chamber that coincides with a position of the detectable area of a rotating element within the housing during at least a portion of the rotating element's rotation cycle. Similarly, the optical detector should be positioned such that it receives light from the portion of the chamber coincident with the portion in the chamber that receives light from the optical emitter. Thus, as optical emitter emits light onto the detectable area of the rotating element, the optical detector can detect the light as it reflects off of the detectable area. Such a configuration allows the optical assembly to provide data to a controller from which rotational information regarding the rotating element, and thus the volume and or velocity of fluid flowing through the meter, can be determined.

In some configurations, it is desirable to position the optical emitter and detector near the meter housing. For example, reducing the distance between the optical emitter and the portion of the housing through which the light is emitted can reduce unwanted reflection of light as it enters the housing. Positioning the emitter and detector proximate the housing can also reduce spreading of light as it propagates into and out of the housing, which can improve the detected signals strength. Accordingly, in some embodiments, at least a portion of the optical assembly is flush against the sidewall of the housing. In further embodiments, both the optical emitter and detector are flush against the sidewall of the housing.

In some embodiments, the capacitive sensor board is configured to accommodate the optical assembly. For example, with reference to FIGS. 8A and 8B, capacitive sensor 820 comprises a hole 862 in the first electrode 822 for accommodating an optical assembly. As shown, the hole 862 is positioned relatively above the oval gear 808. In some embodiments, hole 862 can be positioned relatively above a detectable area on the oval gear 808. In such a configuration, the optical assembly can detect the detectable area on the oval gear 808 through the hole 862. Accordingly, in some embodiments, the optical assembly and capacitive sensor can determine properties of the fluid flowing through the flow meter via the same sidewall of the housing 802. In some embodiments, capacitive sensor 820 can be disposed on a capacitive sensor board, which can include a hole coaxial with the hole 862 in capacitive sensor 820. It should be appreciated that the term "above" as used herein with regard to exemplary embodiments is intended to describe a relative orientation when viewing the figures. In operation, any orientation of the flow meter and associated components is possible.

Figure 11:
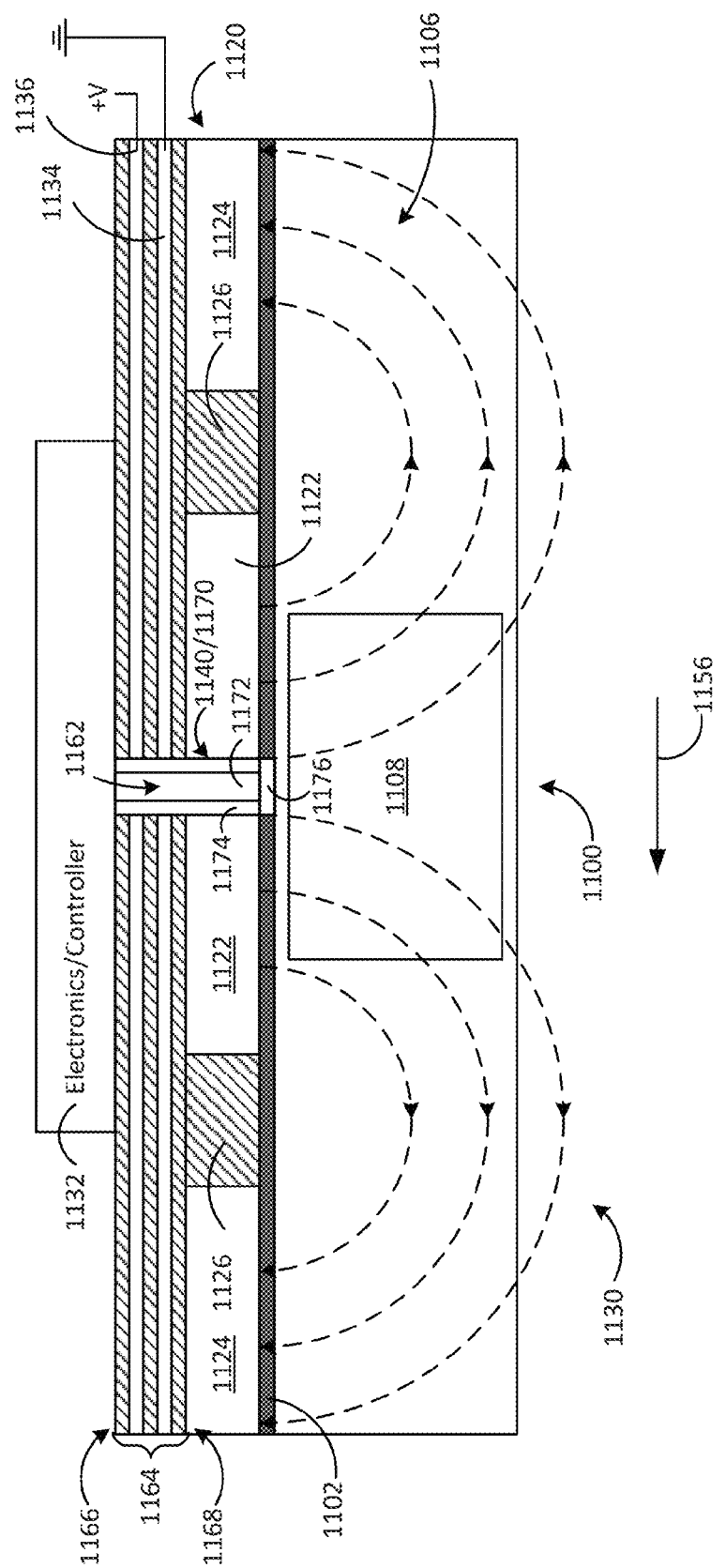
FIG. 11 is a cross sectional view of a system comprising a capacitive sensor such as in FIGS. 8A and 8B comprising integrated electronics and a non-contact sensor.

FIG. 11 is a cross sectional view of a system comprising a capacitive sensor such as in FIGS. 8A and 8B comprising integrated electronics and a non-contact sensor. In the illustrative example of FIG. 11a capacitive sensor 1120 comprising a first electrode 1122 and a second electrode 1124 separated by an insulator 1126 is disposed on the first side 1166 of a capacitive sensor board 1164. Capacitive sensor board 1164 can include power 1136 and ground 1134 layers therein to electrically isolate the capacitive sensor 1120 from electronics 1132 disposed on the second side 1168 of the board 1164. In some embodiments, electronics 1132 can apply an electrical potential between the first electrode 1122 and the second electrode 1124, resulting in an electric field illustrated by field lines 1130.

The capacitive sensor board 1164 is positioned proximate the housing 1102 of a flow meter 1100 which defines a chamber 1106 containing a rotating element 1108. Rotating element 1108 can include, for example an oval gear such as 808 in FIGS. 8A-B. As described elsewhere herein, fluid flowing through the flow meter 1100, in the direction of arrow 1156, for example, can encounter the electric field between the first electrode 1122 and the second electrode 1124. In doing so, the fluid flowing through meter 1100 acts as a dielectric between the electrodes, affecting the capacitance therebetween. In some embodiments, electronics 1132 comprises a controller for detecting the capacitance between the first 1122 and second 1124 electrodes. As described elsewhere herein, such a measurement of capacitance can provide information regarding the fluid flowing through the flow meter 1100 based on the dielectric properties thereof. In some embodiments, the controller can monitor and detect an OOP event based on the capacitance measurement.

As described elsewhere, fluid flowing through the flow meter 1100 can flow past the rotating element 1108 and cause the rotating element 1108 to rotate within the housing 1102. The rotating element 1108 can comprise a detectable area (not shown) which can be detected by a non-contact sensor. The non-contact sensor can provide information to the controller about the rotational motion of the rotating element 1108 from which the controller can determine information regarding the volume and/or the velocity of the fluid through the meter 1100.

In the illustrated embodiment, the non-contact sensor 1140 is be positioned outside of the housing 1102. An exemplary non-contact sensor 1140 disposed outside the housing 1102 can comprise an optical assembly 1170. The optical assembly 1170 can include an optical emitter 1172 and an optical detector 1174 for emitting light into and receiving light from the housing, respectively. While shown in the illustrated embodiment as the optical emitter 1172 being within the optical detector 1174, it should be appreciated that many various configurations are possible. For example, the optical detector 1174 can alternatively be positioned within or beside the optical emitter 1172. In some embodiments, optical assembly 1170 can be controlled by electronics 1132.

As discussed elsewhere herein, it can be advantageous to position the optical emitter 1172 and optical detector 1174 proximate the housing 1102. In the embodiment of FIG. 11, the capacitive sensor board 1164 comprises a hole 1162 therethrough for allowing the optical emitter 1172 and optical detector 1174 to extend therethrough from the electronics 1132 toward the housing 1102. The hole 1162 extends through the power 1136 and ground 1134 layers in the capacitive sensor board 1164, as well as through the first electrode 1122. It will be appreciated that hole can be through any portion of the capacitive sensor board 1164 and any of the first electrode 1122, the second electrode 1124 or the insulator 1126. In some embodiments, the hole 1162 is coincident with the detectable portion of the rotating element 1108 for at least a portion of the rotational motion of the rotating element regardless of which components of the board 1164 the hole 1162 passes through. It should be noted that the capacitive sensor board 1164, including ground 1134 and power 1136 layers, as well as the first electrode 1122, can be continuous around the hole 1162 passing therethrough.

In some such configurations, both the capacitive sensor 1120 and the optical assembly 1170 may be positioned proximate the housing 1102 of the meter 1100. In some embodiments, any of the first electrode 1122, second electrode 1124, optical emitter 1172 and optical detector 1174 can be substantially flush against the housing 1102. The housing 1102 can include a transparent portion 1176, such as a window or transparent sidewall, so that light from the optical emitter 1172 can be emitted through the transparent portion 1176 into the housing, and light from within the housing can be detected by the optical detector 1174 through the transparent portion 1176. In some examples, one or both of the optical emitter 1172 and the optical detector 1174 are substantially flush against the transparent portion 1176 of the housing 1102.

Figure 12:
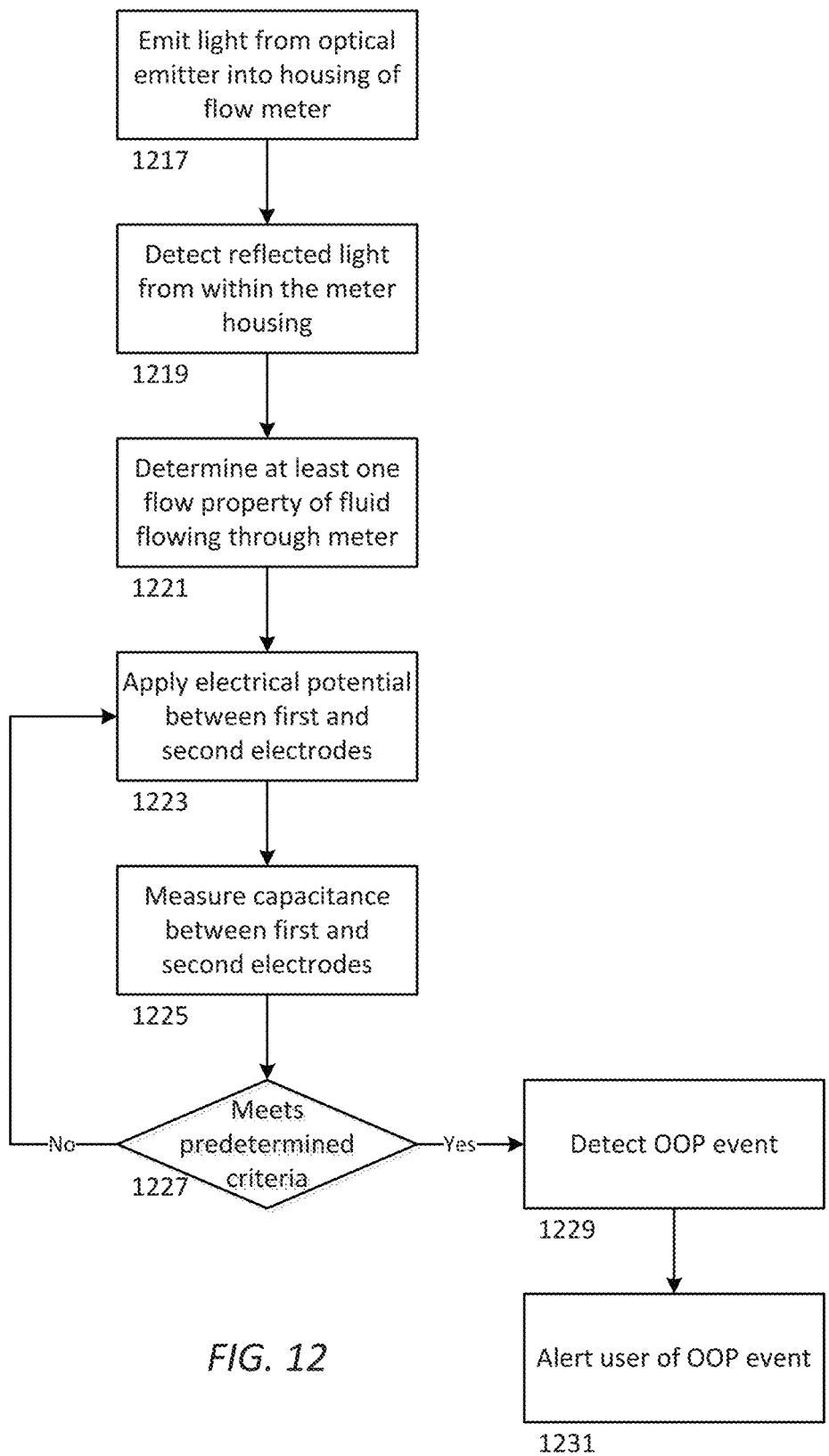
FIG. 12 is a process flow diagram illustrating a method of operating a system comprising capacitive and non-contact sensors.

Accordingly, in some embodiments, a controller can be in communication with the capacitive sensor 1120 and the optical assembly 1170 in order to operate and communicate with each simultaneously. FIG. 12 is a process flow diagram illustrating a method of operating a system comprising capacitive and non-contact sensors. In an exemplary process, a fluid flow meter such as those described herein can be placed in a fluid flow path so that fluid is directed through the fluid flow meter.

During operation, the system can be configured to emit 1217 light from an optical emitter into the housing of the flow meter. In some examples, the light source emits light into the housing via a transparent portion of the housing, such as a window or a transparent sidewall. Light emitted into the housing of the flow meter can reflect back out through the portion of the housing through which it entered. The system can be further configured to detect 1219 reflected light from within the meter housing using an optical detector. As described elsewhere herein, the light detected by the detector can include information indicative of the volume and/or velocity of fluid flowing through the flow meter, for example. The system can accordingly determine 1221 at least one flow property of fluid flowing through the flow meter.

As discussed elsewhere herein, such systems can be equipped with first and second electrodes positioned proximate the flow meter housing. The system can be configured to apply 1223 an electrical potential between the first and second electrodes. Applying 1223 an electrical potential between the first and second electrodes can effect and electric field therebetween which permeates the housing of the flow meter. Thus fluid flowing through the flow meter acts as a dielectric between the first and second electrodes.

The system can measure 1225 the capacitance between the first and second electrodes. Measuring 1225 the capacitance can allow the system to determine information about, for example, the dielectric properties of the fluid. The system can determine 1227 if the capacitance meets a predetermined criteria. In various embodiments, the predetermined criteria can comprise a single criterion or a set of criteria. Criteria can include, for example, the value of the capacitance, the absolute value of the capacitance, or the rate of change of capacitance over time. If the system determines 1227 the capacitance does meet the criteria, the system detects 1229 an OOP event and alert 1231 a user of the OOP event. If not, the system can continue to apply 1223 the electrical potential between the first and second electrodes. As described herein, an OOP event can be detected when the sudden absence of a product in the fluid flowing through the flow meter causes a sudden change in the dielectric properties of the flowing fluid. Such a change will affect the capacitance between the first and second electrodes, which can be detected by the system.

Processes such as that described with regard to FIG. 12 can be initiated and/or executed by a controller. The controller can be in communication with a memory storing predetermined criteria and process information. In some examples, the system can include a user interface for allowing a user to adjust process steps, criteria/thresholds, or other system operation parameters. It will be appreciated that the process illustrated in FIG. 12 is exemplary, and that various steps in the process may be permuted or omitted within the scope of the invention.

The techniques described in this disclosure may be implemented, at least in part, in hardware, software, firmware or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" may generally refer to any of the foregoing logic circuitry, alone or in combination with other logic circuitry, or any other equivalent circuitry. A unit comprising hardware may also perform one or more of the techniques of this disclosure. Such hardware, software, and firmware may be implemented within the same device or within separate devices to support the various operations and functions described in this disclosure.

The techniques described in this disclosure may also be embodied or encoded in a non-transitory computer-readable medium, such as a computer-readable storage medium, containing instructions. Instructions embedded or encoded in a computer-readable storage medium may cause a programmable processor, or other processor, to perform the method, e.g., when the instructions are executed. Non-transitory computer readable storage media may include volatile and/or non-volatile memory forms including, e.g., random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples of the invention have been described. Although the present invention has been described in considerable detail with reference to certain disclosed embodiments, the embodiments are presented for purposes of illustration and not limitation. Other embodiments incorporating the invention are possible. One skilled in the art will appreciate that various changes, adaptations, and modifications may be made without departing from the spirit of the invention and the scope of the appended claims.

The invention claimed is:

1. A system comprising:
a flow meter comprising
(i) a housing including a first sidewall and defining a chamber having a fluid inlet and a fluid outlet wherein at least a portion of the housing is substantially transparent to a first wavelength of light; and
(ii) a first rotating element within the chamber configured to rotate as fluid travels through the housing, wherein the first rotating element comprises a detectable area which reflects light of the first wavelength differently than portions of the first rotating element that are not the detectable areas;
an optical assembly comprising an optical emitter configured to emit light of at least the first wavelength into the chamber via the transparent portion of the housing and an optical detector configured to detect light of at least the first wavelength reflected from inside the chamber; and
a capacitive sensor positioned proximate the housing and substantially flush with the first sidewall, the capacitive sensor comprising a first electrode, a second electrode, and a first insulator separating the first and second electrodes.

2. The system of claim 1, wherein the first and second electrodes are arranged concentrically such that the first electrode is surrounded by the first insulator and the first insulator is surrounded by the second electrode.

3. The system of claim 2, wherein the capacitive sensor is positioned on a capacitive sensor board external to and abutting the first sidewall of the housing.

4. The system of claim 3, wherein the area spanned by the capacitive sensor is approximately equal to the size of the first sidewall.

5. The system of claim 4, wherein the portion of the housing that is substantially transparent to the first wavelength of light is positioned on the first sidewall of the housing.

6. The system of claim 5, wherein the substantially transparent portion of the first sidewall comprises sapphire.

7. The system of claim 5, where the capacitive sensor comprises at least one hole in any of the first electrode, the second electrode, or the insulator, the at least one hole positioned such that when the first rotating element is rotated within the chamber, the position of the detectable area of the first rotating element coincides with the position of the hole in the capacitive sensor during a portion of the rotation.

8. The system of claim 7, wherein the optical emitter and optical detector are positioned in the at least one hole in the capacitive sensor such that the optical emitter, optical detector, and first and second electrodes are substantially flush with the first sidewall of the housing.

9. The system of claim 8, further comprising a controller configured to
receive a detection signal from the first non-contact sensor representative of the rotational position of the first rotating component;
determine, from the detection signal, at least one of a volume or flow rate of fluid passing through the flow meter;
apply an electrical potential between the first and second electrodes of the first capacitive sensor;
determine the capacitance between the first and second electrodes; and
based on the determined capacitance, detect the presence of a product flowing through the housing.

10. The system of claim 9, wherein the capacitive sensor is positioned on a first side of the capacitive sensor board, the first side of the capacitive sensor board facing the first sidewall of the housing; and wherein
the capacitive sensor board comprises a second side, opposite the first, and a ground layer and a powered layer each positioned between the first and second sides of the capacitive sensor board.

11. The system of claim 10, further comprising electronic circuitry for interfacing with at least one of the capacitive sensor or the optical assembly.

12. The system of claim 11, wherein the controller is positioned on the second side of the capacitive sensor board.

13. The system of claim 10, further comprising a reference capacitive sensor positioned on the capacitive sensor board and configured to detect a reference capacitance.

14. The system of claim 13, wherein the reference capacitive sensor is positioned on the second side of the capacitive sensor board.

15. A system comprising:
a flow meter comprising
a housing defining a chamber having a fluid inlet and a fluid outlet wherein at least a portion of the housing is substantially transparent to a first wavelength of light; and
a first rotating element within the chamber configured to rotate as fluid travels through the housing, wherein the first rotating element comprises a detectable area which reflects light of the first wavelength differently than portions of the first rotating element that are not the detectable areas;
an optical assembly comprising an optical emitter configured to emit light of at least the first wavelength into the chamber via the transparent portion of the housing and an optical detector configured to detect light of at least the first wavelength reflected from inside the chamber; and
a capacitive sensor comprising:
a first electrode;
a second electrode;
a first insulator separating the first and second electrodes; and at least one hole in any of the first electrode, the second electrode, or the insulator; wherein the capacitive sensor is positioned on a capacitive sensor board external to the housing; and the at least one hole in the capacitive sensor is positioned such that when the first rotating element is rotated within the chamber, the position of the detectable area of the first rotating element coincides with the position of the hole in the capacitive sensor during a portion of the rotation.

16. The system of claim 15, wherein the optical emitter and optical detector are positioned in the at least one hole in the capacitive sensor such that the optical emitter, optical detector, and first and second electrodes are substantially flush with the first sidewall of the housing.

17. The system of claim 15, further comprising a controller configured to receive a detection signal from the first non-contact sensor representative of the rotational position of the first rotating component;

determine, from the detection signal, at least one of a volume or flow rate of fluid passing through the flow meter;

apply an electrical potential between the first and second electrodes of the first capacitive sensor;

determine the capacitance between the first and second electrodes; and based on the determined capacitance, detect the presence of a product flowing through the housing.

18. The system of claim 15, wherein the capacitive sensor is positioned on a first side of the capacitive sensor board, the first side of the capacitive sensor board facing the first sidewall of the housing; wherein the capacitive sensor board comprises:

a second side, the second side being opposite the first side, a ground layer, and a powered layer; wherein the ground layer and the powered layer are each positioned between the first side and the second side of the capacitive sensor board.

19. The system of claim 18, further comprising electronic circuitry positioned on the second side of the capacitive sensor board, the electronic circuitry being in electrical communication with at least one of the capacitive sensor or the optical assembly.

20. The system of claim 15, further comprising a reference capacitive sensor positioned on the capacitive sensor board and configured to detect a reference capacitance.

\* \* \* \* \*